United States Patent
Commarieu et al.

[11] Patent Number: 6,123,850
[45] Date of Patent: *Sep. 26, 2000

[54] PROCESS FOR THE PURIFICATION OF VIRTUALLY ANHYDROUS ORGANIC LIQUIDS

[75] Inventors: Annie Commarieu, Courbevoie; Francis Humblot, Lanneplaa, both of France

[73] Assignee: Elf Atochem, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 09/078,480

[22] Filed: May 14, 1998

[30] Foreign Application Priority Data

May 15, 1997 [FR] France .................... 97 05966

[51] Int. Cl.$^7$ .............. B01J 39/00; B01J 49/00; B01J 47/02; C02F 1/42; B01D 15/04
[52] U.S. Cl. ............ 210/662; 210/638; 210/669; 210/670; 210/672; 210/681; 210/683; 210/684; 210/685; 210/688
[58] Field of Search ................. 210/662, 669, 210/670, 681, 683, 684, 685, 688, 686, 672

[56] References Cited

U.S. PATENT DOCUMENTS

| | | | |
|---|---|---|---|
| 3,505,005 | 4/1970 | Gilbert | 8/142 |
| 4,190,532 | 2/1980 | Halbfoster | 210/75 |
| 4,747,954 | 5/1988 | Vaughn et al. | 210/670 |
| 4,795,565 | 1/1989 | Yan | 210/669 |
| 5,162,084 | 11/1992 | Cummings et al. | 210/662 |
| 5,284,930 | 2/1994 | Matsumoto et al. | 528/482 |
| 5,288,850 | 2/1994 | Matsumoto et al. | 528/482 |
| 5,500,127 | 3/1996 | Carey et al. | 210/685 |
| 5,518,628 | 5/1996 | Carey | 210/686 |
| 5,525,315 | 6/1996 | Burke | 423/24 |
| 5,571,657 | 11/1996 | Szmanda et al. | 430/270.1 |

FOREIGN PATENT DOCUMENTS

| | | |
|---|---|---|
| 306261 | 3/1989 | European Pat. Off. . |
| 412214 | 2/1991 | European Pat. Off. . |
| 4308569 | 9/1984 | Germany . |
| 55-160744 | 12/1980 | Japan . |
| 61-171507 | 2/1986 | Japan . |
| 2032655 | 4/1995 | Russian Federation . |
| 2088850 | 6/1982 | United Kingdom . |
| 97/19057 | 5/1997 | WIPO . |
| WO 98/04348 | 2/1998 | WIPO . |

OTHER PUBLICATIONS

Buragohain et al) "Novel Resin–Based Ultrapurification System for Reprocessing IPA in the Semiconductor Industry", Ind.Eng.Chem. Res. 1996, vol. 35, pp. 3149–3154.

"Removal of electrically conducting impurities from alcohols by ion exchange", Myakon'kii, et al., Vysokochist Veshchestva, vol. 2, pp. 71–75 (1992).

"On the Extraction of Various Base Metal Chlorides From Polar Organic Solvents Into Cation and Anion Exchange Resins", C.A. Fleming, et al.Hydrometallurgy, vol. 4, pp. 159–167 (1979).

*Primary Examiner*—Floyd D. Higel
*Attorney, Agent, or Firm*—Smith Gambrell & Russell, L.L.P.

[57] ABSTRACT

The subject matter of the present invention is a process for the purification of a virtually anhydrous organic liquid other than DMSO alone, in order to decrease its content of alkali and alkaline-earth metal and metal cations, characterized in that it consists essentially in placing this organic liquid in contact with one or more cation exchange resins and in then separating from the resin(s) the purified organic liquid, said resin or at least one of said resins being a sulphonic resin in —$SO_3H$ or —$SO_3NH_4$ form based on a polystyrene-divinylbenzene copolymer having a divinylbenzene content of from 50 to 60% by weight, without taking the sulphonic groups into account.

8 Claims, No Drawings

PROCESS FOR THE PURIFICATION OF VIRTUALLY ANHYDROUS ORGANIC LIQUIDS

FIELD OF THE INVENTION

The present invention relates to the purification of virtually anhydrous liquids consisting of one or more organic compounds and its subject-matter is more particularly a process for removing the metallic impurities present in such liquids.

BACKGROUND OF THE INVENTION

The majority of commercial organic liquids are available on the market in a purity which is already very high, generally higher than 99%. However, as the data in Table 1 show, metals in trace form are still found in these liquids, which require an additional purification to permit their use in industries such as electronics or pharmacy. In general, organic liquids containing less than 10 ppb of each alkali and alkaline-earth metal and metal contaminant would be necessary for most of the uses in these two technical fields (1 ppb=1 part by weight per thousand million, that is 1 μg per kg).

TABLE 1

| Compound | 1-methyl-2-pyrrolidone | isopropyl alcohol | N,N-dimethyl-acetamide | mono-ethanol-amine | benzyl alcohol |
|---|---|---|---|---|---|
| Supplier | S.G.S. | S.D.S. | Aldrich | Hüls | Elf Atochem |
| Grade | ultra-pure | purex for analysis | H.P.L.C. | ultra-pure | photo-graphic grade |
| Purity (%) | 99.95 | 99.7 | 99.9 | 99.90 | 99.90 |
| Water (%) | 0.02 | 0.1 | <0.03 | 0.06 | <0.1 |

| Metal | Detection limit (ppb) | Content as metal (ppb) | | | | |
|---|---|---|---|---|---|---|
| Na | 2 | 30 | 30 | 150 | 20 | 240 |
| Fe | 1 | 15 | 6 | 85 | 5 | 5 |

It therefore appears desirable to have available a process for the purification of commercial liquids containing one or more organic compounds, which are already of a good purity, but nevertheless insufficient for some applications, this process being aimed especially at reducing their content of traces of metals.

Ion exchange resins are very commonly employed nowadays for deionizing water. On the other hand, their use in an organic medium appears to be markedly less widespread or investigated. This absence of development owes its origins to the special properties of water, which ionizes salts and separates the anions completely from the cations. On the other hand, depending on the dielectric constant of the organic medium, the ions formed by ionization are found to be more or less dissociated and more or less free to exchange with the functional groups of the resin.

Nevertheless some published research is found (C. A. Fleming and A. J. Monhemus, Hydrometallurgy, 4, pp. 159–167, 1979), the objective of which is to improve by a solvent effect the selectivity of exchange of some metals with cationic resins, the final aim being to determine the conditions which permit the separation of the metals in preparative ion chromatography. These studies describe exchange isotherms, that is to say the laws which govern the equilibrium between the metal ion in solution and the metal ion bound to the resin. The usual conditions of such work consequently remain very far from a method of deionization of an organic medium.

U.S. Pat. No. 4,795,565 describes the purification of an aqueous solution of ethanolamine on an ion exchange resin. The objective of this patent is the removal of some salts produced during the ethanolamine extraction of carbon dioxide and hydrogen sulphide present in refinery gases. The spent ethanolamine solution containing between 80 and 50% water by weight is passed successively over a stationary bed of strong anionic resin and then over a stationary bed of strong cationic resin. U.S. Pat. No. 5,162,084 relates to the same type of application, but improves the purification efficiency by employing a combination of two anionic resins and by judiciously controlling the operation of the unit with the aid of conductimetric sensors. These patents do not describe the purification of ethanolamine with a low water content on ion exchange resins.

Patent GB 2 088 850 describes the purification of 1-methyl-2-pyrrolidone (NMP) by passing over an anionic resin binding the chloride and carboxylic ions. This treatment is inserted into a process of selective extraction with NMP of the aromatic hydrocarbons present in a mixture of paraffins. No purification with cationic resins is described in this patent. Furthermore, 10% of water by weight is advantageously added to the NMP to improve the selectivity of extraction.

Patent RU 2 032 655 relates to the deionization of aliphatic alcohols or of diols with the aim of reducing their electric conductivity. For this purpose the authors employ a stationary bed of anionic resin and of cationic resin in equal proportions, these resins being saturated with water beforehand. In a subsequent publication (Vysokochist. Veshchestva, 2, pp. 71–75, 1992), A. G. Myakon'kii et al. have indicated that a minimum water content of 2.5% in the medium is necessary to obtain deionization with the aid of the pair of dry resins.

In an article intitled "Novel resin-based ultrapurification system for reprocessing IPA in the semiconductor industry" (Ind. Eng. Chem. Res. 1996, 35, 3149–3154), P. V. Buragohain et al. propose using cation exchange resins (Amberlite® IR 120, Dowex® M31 and Ionac® CFP 110) to purify isopropylic alcohol (IPA). In these cationic resins, the divinylbenzene content in the copolymer does not exceed 20%.

The use of an ion exchange resin of sulphonic type which has its active groups in $SO_3H$ acidic form for the purification of dimethyl sulphoxide (DMSO) forms the subject matter of the patent application WO97/19057 published on May 29, 1997.

DESCRIPTION OF THE INVENTION

It has now been found that the use of a cationic resin of sulphonic type based on a polystyrene-divinylbenzene copolymer having a high content of divinylbenzene allows, in a virtually anhydrous organic liquid, to retain and exchange any cation $M^{n+}$ (n having values from 1 to 4) with n $H^+$ protons or with n $NH_4^+$ ions of such a resin in protonic or ammonium form.

The subject matter of the present invention is therefore a process for the purification of a virtually anhydrous organic liquid other than DMSO alone, in order to decrease its content of alkali and alkaline-earth metal and metal cations, characterized in that it consists essentially in placing this organic liquid in contact with one or more cation exchange resins and in then separating from the resin(s) the purified organic liquid, said resin or at least one of said resins being a sulphonic resin in —$SO_3H$ or —$SO_3NH_4$ form based on a polystyrene-divinylbenzene copolymer having a divinylbenzene content of from 50 to 60% by weight, without taking the sulphonic groups into account.

A virtually anhydrous organic liquid is here intended to mean an organic liquid which has a water content lower than or equal to 1% by weight, preferably lower than or equal to 0.15% by weight.

The process according to the invention can be applied in order to purify any liquid organic compound which exhibits a dielectric constant ε ranging from 5 to 50 and a pKa higher than 2. Nonlimiting examples of such compounds which may be mentioned more particularly are 1-methyl-2-pyrrolidone (NMP), isopropyl alcohol (IPA), benzyl alcohol (BYA), dimethylacetamide (DMAC), monoethanolamine (MEA), ethyl acetate, butyl acetate, ethyl lactate, butyl lactate, tetrahydrothiophene 1,1-dioxide (sulfolane), glycerol, acetic acid, acetone and propylene glycol monomethyl ether acetate (PGMEA). The process is also suitable for the purification of mixtures of these compounds with each other or with DMSO in very variable proportions. Nonlimiting examples of such mixtures which may be mentioned are more particularly DMSO/MEA, NMP/MEA, DMSO/BYA and DMSO/BYA/MEA mixtures.

Cation resins which can be used for implementing the process according to the invention are well-known products and are commercially available, especially under the names Amberlyst® and XN 1010 (marketed by Rohm & Haas), Hypersol Macronet® (marketed by Purolite) and Relite® (marketed by Mitsubishi).

At least one of the resins used in accordance with the invention is a sulphonic resin based on a polystyrene-divinylbenzene copolymer wherein the divinylbenzene represents from 50 to 60% by weight and the polystyrene from 50 to 40% by weight relative to the total weight of the copolymer, without taking the sulphonic groups into account. This ratio of divinylbenzene ensures a good kinetic activity of the exchange of the $M^{n+}$ cations with the n $H^+$ protons or the n $NH_4^+$ cations.

When several resins are employed, at least one of these resins is such as defined above, it being possible for the other(s) to be of chelating type. The organic liquid to be purified may be placed in contact with a mixture of the various resins or successively with each of the various resins.

The contact of the organic liquid to be purified with the resin(s), preferably in the $H^+$ form, is brought about at a temperature ranging from the melting point of the liquid to be purified to 120° C. (thermal stability limit temperature of the resins). This temperature is advantageously between 19 and 80° C., preferably between 20 and 50° C.

The operation may be carried out noncontinuously (batchwise) or continuously, in conditions and equipment which are well known to a person skilled in the art. The separation of the purified liquid from the resin(s) can be done by any appropriate known means, especially by filtration, percolation or centrifuging.

EXAMPLES

The invention will be understood better with the aid of the following experimental part describing examples of implementation of the present invention.

Experimental Part

I. Methodology

The trace metals are in $M^{n+}$ form. On contact of the liquid to be purified with the cation exchange resin or resins, themselves in $H^+$ or $NH_4^+$ form, the $M^{n+}$ ions in solution are replaced with $H^+$ protons or with $NH_4^+$ ions.

In a first step, batchwise tests were carried out to treat various organic compounds, which were pure or mixed.

In a second step, some media were purified continuously, by passing the liquid over a stationary bed of ion exchange resin. This technique is actually more satisfactory and representative of a real production of purified liquid.

II. Method of Analysis

The method of analysis of trace metals in organic media is I.C.P. (plasma torch—atomic emission spectrometry): the sample is introduced into a plasma torch, where the various elements are excited and emit photons whose energy is characteristic of the element, since it is defined by the electron structure of the element in question. A Perkin Elmer instrument (Optima 3000 DV model) was employed routinely.

This technique allows the content of several metals to be analysed simultaneously. For the sake of clarity of the results, it was chosen to indicate only the content of iron and of sodium, which are tracers representing all the metallic impurities present. Sodium reflects an atmospheric and accidental contamination (dust) and iron is characteristic of a contamination originating from the process of manufacture or from packaging (contact of the liquid with steel).

The detection limits of this technique of analysis depend on the metal in question. In the case of sodium the detection limit is 2 ppb and in the case of iron 1 ppb.

III. Batchwise Tests

III.1. Experimental Preparation

Between 100 and 1000 ppb of sodium and iron were added to 100 g of organic liquid and this solution was then placed in contact with a known quantity of resin (between 2 and 10 g) in $H^+$ form. Samples of liquid were taken in the course of time in order to follow the change in the iron and sodium concentrations.

The resin employed (Hypersol Macronet® MN 500 supplied in $H^+$ form by Purolite) is a sulphonic resin with a styrene/divinylbenzene structure. It was dried beforehand by suspension in methanol and evaporation under vacuum in the rotary evaporator (90° C., 2000 Pa) until a constant weight was observed.

III.2. Reduction in the Cation Content (other than $H^+$) of NMP: Example 1

The effectiveness of the MN 500 resin was tested in the purification of NMP by employing 10 g of resin per 100 g of NMP. The change in the iron and sodium contents in the course of time are collated in Table 2.

TABLE 2

| | Example 1 | | | |
|---|---|---|---|---|
| Time (hr) | 0 | 4 | 8 | 24 |
| [Na] (ppb) | 110 | <2 | <2 | <2 |
| [Fe] (ppb) | 100 | 3 | <1 | <1 |

III.3. Reduction in the Cation Content (other than $H^+$) of Various Pure or Mixed Organic Media: Examples 2 to 12

The efficiency of the ion exchange between a resin and an organic medium depends on the nature of the resin and also on the medium in question. In Examples 2 to 9 the activity of Purolite MN 500 sulphonic resin was tested with regard to the cations present in various pure organic media or mixtures of organic compounds. Table 3 (Example 2) shows the change in the iron and sodium concentration as a function of time in benzyl alcohol treated with 2% by weight of MN 500 resin.

TABLE 3

Example 2

| Time (min) | 0 | 5 | 10 | 20 | 25 | 30 | 45 | 60 | 90 | 120 |
|---|---|---|---|---|---|---|---|---|---|---|
| [Na] (ppb) | 450 | 200 | 80 | 40 | 20 | 18 | 10 | 10 | 8 | 8 |
| [Fe] (ppb) | 530 | 440 | 340 | 280 | 150 | 130 | 110 | 60 | 12 | 10 |

Collated in Table 4 (Examples 3 to 7) are the results relating to the kinetics of exchange of iron and sodium in five other organic compounds: isopropyl alcohol (IPA), N,N-dimethylacetamide (DMAC), monoethanolamine (MEA), propylene glycol monomethyl ether acetate (PGMEA) and acetic acid (AcOH).

IV. Continuous Tests

IV.1. Experimental Preparation

Starting from the batchwise results, several continuous tests were undertaken according to the rules commonly followed by a person skilled in the art with regard to the column diameter/particle size and column height/column diameter ratios and to the linear velocity, in order not to have a limitation related to diffusion.

The resin pretreated as indicated above is suspended in 90 ml of liquid in a beaker and gently stirred (to remove air bubbles). This suspension is introduced into a column made of Teflon, in vertical position, and the lower part of which is equipped with a polyethylene sinter of 70 $\mu$m porosity. The beaker is rinsed with 10 ml liquid. Under the sinter the column is equipped with a Teflon stopcock. This stopcock is closed during the filling operation. Once the resin has been deposited and packed down in the column, the stopcock is opened and the column is fed continuously with medium to be purified by virtue of a pump equipped with a Teflon head. Samples are taken at regular intervals. All the pipes and couplings are made of Teflon. The bottles are made of high density polyethylene.

TABLE 4

Examples 3 to 7

| Example No. | 3 | | 4 | | 5 | | 6 | | 7 | |
|---|---|---|---|---|---|---|---|---|---|---|
| Organic liquid | IPA | | DMAC | | MEA | | PGMEA | | AcOH | |
| Amount of resin (% w/w) | 5 | | 5 | | 5 | | 10 | | 10 | |
| Time (hours) | [Na] (ppb) | [Fe] (ppb) | [Na] (ppb) | [Fe] (ppb) | [Na] (ppb) | [Fe] (ppb) | [Na] (ppb) | [Fe] (ppb) | [Na] (ppb) | [Fe] (ppb) |
| 0 | 250 | 240 | 530 | 570 | 100 | 100 | 30 | 40 | 420 | 100 |
| 1 | 5 | 36 | 5 | 70 | 20 | 3 | 22 | 20 | 30 | 6 |
| 2 | 3 | 6 | 2 | 30 | 12 | 2 | 20 | 12 | 19 | 3 |
| 4 | 2 | 5 | <2 | 15 | 10 | <2 | 19 | 9 | 15 | 2 |
| 6 | 3 | 6 | 2 | 13 | 8 | 2 | — | — | — | — |
| 8 | 2 | 7 | <2 | 10 | 3 | 2 | 10 | 7 | 10 | 3 |
| 24 | — | — | — | — | — | — | 9 | 6 | 7 | 2 |

The exchange kinetics of sodium and of iron in binary mixtures of organic compounds are collated in Table 5. The same resin as previously (MN 500) was employed.

TABLE 5

Examples 8 to 12

| Example No. | 8 | | 9 | | 10 | | 11 | | 12 | |
|---|---|---|---|---|---|---|---|---|---|---|
| Mixture | DMSO/MEA 70/30 (w/w) | | DMSO/MEA 30/70 (w/w) | | NMP/MEA 70/30 (w/w) | | NMP/MEA 30/70 (w/w) | | DMSO/BYA 50/50 (w/w) | |
| Quantity of resin (% w/w) | 5 | | 5 | | 5 | | 5 | | 5 | |
| Time (hours) | [Na] (ppb) | [Fe] (ppb) | [Na] (ppb) | [Fe] (ppb) | [Na] (ppb) | [Fe] (ppb) | [Na] (ppb) | [Fe] (ppb) | [Na] (ppb) | [Fe] (ppb) |
| 0 | 160 | 270 | 150 | 210 | 155 | 170 | 125 | 170 | 500 | 600 |
| 8 | <2 | 9 | 10 | 13 | 2 | 6 | <2 | 9 | <2 | 7 |
| 24 | 2 | 5 | 8 | 9 | 2 | 3 | <2 | 4 | <2 | 9 |

IV.2. Reduction in the Cation Content (other than H⁺) of Various Media Consisting of One or More Organic Products: Examples 13 to 16

MN 500 resin

Volume of dry resin: 35 cm³

(except Example 16: 88 cm³)

Particle size: 0.3 to 1.2 mm

The results appear in Table 6, which follows. The equivalent volume, which expresses the change in the test is the ratio of the volume of liquid (in litres) to the volume of resin (in ml).

TABLE 6

Examples 13 to 16

| | | | | | | | | |
|---|---|---|---|---|---|---|---|---|
| Example 13 | Equivalent volume | 0 | 0.49 | 2.8 | 3.6 | 5.6 | 6.5 | 7.2 |
| | | | | | | | | |
| DMSO/MEA | [Na] (ppb) | 26 | 4 | 5 | 4 | 5 | 4 | 3 |
| 70/30 (w/w) | [Fe] (ppb) | 9 | 7 | 8 | 7 | 7 | 7 | 7 |
| Example 14 | Equivalent volume | 0 | 0.31 | 2.3 | 3.13 | 5.2 | 7.4 | 8.14 |
| | | | | | | | | |
| DMSO/MEA | [Na] (ppb) | 40 | <2 | <2 | <2 | <2 | <2 | <2 |
| 30/70 (w/w) | [Fe] (ppb) | 33 | 20 | 12 | 7 | <1 | <1 | <1 |
| Example 15 | Equivalent volume | 0 | 0.45 | 2.7 | 3.4 | 5.8 | 6.1 | 6.9 |
| | | | | | | | | |
| NMP/MEA | [Na] (ppb) | 27 | 5 | 5 | 5 | 5 | 5 | 5 |
| 70/30 (w/w) | [Fe] (ppb) | 5 | 3 | 2.5 | 1 | 1 | 1 | 1 |
| Example 16 | Equivalent volume | 0 | 0.07 | 0.12 | | | | |
| | | | | | | | | |
| n-Butyl | [Na] (ppb) | 140 | 3 | 2 | | | | |
| acetate | [Fe] (ppb) | 9 | 2 | 2 | | | | |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for purification of a virtually anhydrous organic liquid other than dimethyl sulphoxide alone, to decrease its content of alkali and alkaline-earth metal and metal cations, comprising placing the organic liquid to be purified in contact with at least one cation exchange resin in acidic or ammonium form and then separating from the resin the purified organic liquid, said resin or at least one of the resins being a sulphonic resin in —$SO_3H$ or —$SO_3NH_4$ form based on a polystyrene-divinylbenzene copolymer having a divinylbenzene content of from 50 to 60% by weight, without taking the sulphonic groups into account, the water content of the organic liquid being lower than or equal to 1% by weight.

2. Process according to claim 1, wherein that in that the liquid to be purified is an organic compound exhibiting a dielectric constant ε ranging from 5 to 50 and a pKa higher than 2, or a mixture of such compounds with each other and/or with dimethyl sulphoxide (DMSO).

3. Process according to claim 2, wherein the liquid to be purified is selected from 1-methyl-2-pyrrolidone (NMP), isopropyl alcohol, benzyl alcohol (BYA), dimethylacetamide, monoethanolamine (MEA), ethyl acetate, butyl acetate, ethyl lactate, butyl lactate, sulfolane, gylcerol, acetic acid, acetone, propylene glycol monomethyl ether acetate and DMSO/MEA, DMSO/BYA and DMSO/BYA/MEA mixtures wherein DMSO is dimethyl sulphoxide.

4. Process according to claim 1, wherein at least two resins are used, at least one of which is a sulphonic resin such as defined in claim 1 and the other(s) optionally a chelating resin.

5. Process according to claim 1, wherein the at least one resin is in the H⁺ form.

6. Process according to claim 1, wherein the contact of the liquid to be purified with the exchange resin(s) takes place at a temperature ranging from 19 to 80° C.

7. Process according to claim 6 wherein the temperature is between 20 and 50° C.

8. Process according to claim 1, wherein the water content is less than or equal to 0.15% by weight.

* * * * *